United States Patent
Lang (10) Patent No.: US 7,676,272 B2
(45) Date of Patent: Mar. 9, 2010

(54) IMPLANTABLE DEVICE SYSTEM TO COLLECT PARAMETER DATA FOR SERVICE CENTER

(75) Inventor: Volker Lang, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 204 days.

(21) Appl. No.: 11/782,537

(22) Filed: Jul. 24, 2007

(65) Prior Publication Data

US 2009/0030487 A1   Jan. 29, 2009

(51) Int. Cl.
*A61N 1/37*   (2006.01)
*A61N 1/18*   (2006.01)

(52) U.S. Cl. .................. 607/60; 340/573.1; 600/300; 128/905; 607/2; 607/63

(58) Field of Classification Search ............. 340/573.1; 607/9, 17, 25, 26, 30–32, 59, 60, 63; 705/2–3; 600/509, 512, 515
See application file for complete search history.

(56) References Cited

U.S. PATENT DOCUMENTS 5,642,734 A * 7/1997 Ruben et al. ................. 600/506

2005/0231374 A1 * 10/2005 Diem et al. ............... 340/573.1

* cited by examiner

*Primary Examiner*—Carl H Layno
*Assistant Examiner*—Pamela M Bays
(74) *Attorney, Agent, or Firm*—Dalina Law Group, P.C.

(57) ABSTRACT

An implantable device system comprising an implantable medical device, an external transceiver device and a service center. The implantable medical device comprises a battery and an electronic module including a stimulation pulse generator, a sensing stage, a control unit adapted to collect data representing values of operational parameters (e.g. peak or average current consumption, high/low/average voltage level) of the battery and the electronics. The external transceiver device comprises an external transceiver unit and a data communication interface and the service center comprises another data communication interface adapted to allow data communication with the external transceiver device. Service center includes a central database adapted to store data received from the external transceiver per implantable medical device over time, a data evaluation module adapted to evaluate including trending of data stored in the database and a user interface adapted to display trended data and to receive user inputs.

11 Claims, 4 Drawing Sheets

IMPLANTABLE DEVICE SYSTEM TO COLLECT PARAMETER DATA FOR SERVICE CENTER

BACKGROUND OF THE INVENTION

1. Field of the Invention

The invention relates to an implantable device system comprising an implantable medical device, an external transceiver device and a service center.

The implantable medical device preferably is an implantable pacemaker or an implantable cardioverter/defibrillator (ICD), or a device for cardiac resynchronization (CRT-D).

2. Description of the Related Art

Implantable medical devices are very complex products consisting of energy sources (batteries), electronic modules with one or more micro-processors, embedded software running on those processors, high voltage units (in ICD and CRT-D), memory IC's, IC for signal detection, IC for signal analysis (DSP), components for therapy, component for communication, storage for therapeutic fluids (drug pumps) and others. Even so the reliability of those implantable medical devices is in general very high, failures may potentially happen, especially for highly complex implantable medical devices with long service times of more than 1 year.

The specific problem of medical devices is that due to their constraints of size and service-time often real redundancy is not possible, e.g. if the high voltage units in ICD fail, there is not a second set of high voltage capacitors to compensate for the failure. However, most of the time the implantable medical device does not have to support life critical functions permanently. Therefore, to increase the safety for the patients, it is more than appropriate to detect the failure early enough and mitigate the problem before a life critical support is necessary.

BRIEF SUMMARY OF THE INVENTION

It is an object of the invention to provide a technical solution to detect failures in implantable devices early with remote monitoring.

According to the invention this objective is achieved by a medical device system comprising several parts distributed over different subparts of a medical device system including an implantable medical device, an external transceiver and a service center.

The implantable medical device comprises a battery and an electronic module including At least a stimulation pulse generator adapted to generate electric stimulation pulses and being connected or being connectable to at least a ventricular stimulation electrode for delivering electric stimulation pulses to at least said ventricle of the heart, at least one internal sensor that is connected to said battery, said stimulation pulse generator and said sensing stage and that is adapted to collect physical data representing values of operational parameters of said battery and said electronic module including said control unit, a sensing stage connected or being connectable to an electrode for picking up electric potentials inside at least a ventricle of a heart, said sensing stage being adapted to sense an excitation or a contraction of ventricular myocardium, a control unit that is connected to said battery, said stimulation pulse generator and said sensing stage and that is adapted to collect data representing values of operational parameters of said battery and said electronic module including said control unit, and an implant transceiver unit for wireless communication with the external transceiver device.

The implantable medical device is adapted to collect data that represent measurements of one or more values of one or more parameters of the following operational parameters of the battery and/or the electronic module and/or the electronic components on the module per settable time-unit:

peak current consumption, average current consumption, high/low/average voltage level, charge counter for battery status, programmed versus actual pacing voltage in at least one pacing channel, programmed versus actual shock energies if a defibrillation shock generator is available, charging times, impedance of all pacing and shock electrodes, status of embedded software, in particular number of CPU cycles, number of memory accesses, number of resets; number of read/write errors; number of hypo- and hyper-watchdog errors; number of recoverable and non-recoverable memory corruptions, actual service time, temperature, temperature rise during high-voltage operations, pressure, impedance of components such as resistors, capacitors, self-diagnostic information of the IC like range checks and to transmit the data to the external transceiver.

The external transceiver device comprises an external transceiver unit for wireless communication with the implant transceiver unit and a data communication interface adapted to allow a data communication with the service center. The external transceiver is adapted to collect automatically data from device and to transmit them to the central service center. Further the external receiver preferably is adapted to transfer the data collected from the implantable medical device and add its own data set including data representing measurements relating to at least one value of one or more of the following parameters:

peak current consumption, average current consumption, high/low/average voltage level, number of charging cycles, number of successful/dropped/repeated MICS communications, number of successful/dropped/repeated Landline/SMS/GPRS/UMTS connections, number of corrupted data packages.

The service center comprises another data communication interface adapted to allow data communication with said external transceiver device, and a central database for data storage and automatic data analysis that is adapted store data received from the external transceiver per implantable medical device over time, and a data analysis module for early failure detection, wherein the data analysis module is adapted to perform a data analysis in four different levels:

(1) each value/parameter against specification;
(2) each value is trended and checked against unexpected changes and shifts (e.g. increase of battery voltage);
(3) each value is checked if its measurements represent an outlier as compared to all comparable devices (e.g. charging time of one device is within its specification but far outside the normal population);
(4) every value is ranked against values other devices to identify the "worst".

The implantable medical device and the external transceiver are preferably adapted to generate and transmit one data set per day.

With respect to the data analysis according to level (1) it is preferred that the data analysis module is adapted to compare all measurements (currents, voltages, impedance, . . . ) against predetermined specifications and to set a flag for each out-of-spec value if the actual value is outside the predetermined specifications.

With respect to the data analysis according to level (2) it is preferred that the data analysis module is adapted to trend all measurements over time and to set an unexpected change flag in case of detection of any unexpected change, e.g. $dM_i/dt$>threshold$_i$. Preferably, for values which are not expected to change then a change of >10% is considered significant, that is, an unexpected change flag is set if a change >10% is detected in the trended data.

Preferably, the data analysis module is further adapted to compute consistency checks, e.g. battery voltage level versus charge counter value, when performing a data analysis according to level (2) or (3).

Preferably, the data analysis module is further adapted to perform a comparison between devices if more than n=27 comparable devices are available. The analysis preferably comprises one or more of the following computations:

For all measurements i of all comparable devices j compute average Ai+standard deviation σi; identify devices, for which measurements are outside 3*σi For all measurements i of all comparable devices j compute the rank Ri; identify devices, for which measurements are >9th percentile Other statistical techniques to identify outliers Further, the data analysis module is preferably adapted to perform a comparison of measurements of devices which share same component j, e.g. batteries from vendor A, as follows:

For all measurements i of all comparable components k compute average Ai+standard deviation σi; identify devices, for which measurements are outside 3*σi The service center preferably further comprises a data mining system that can be used if the measurements, trends, averages, etc. represent multidimensional data which need to be condensed more. The data mining system is preferably adapted to classify devices which fail one criteria (e.g. voltage level too low), two criteria (e.g. voltage level too low and charging time is increasing over time), etc. to flag devices which fail an increasingly number of criteria.

The service center preferably further comprises an expert system to further compute the analyzed data. The expert system implements a rule system to identify previously noted problems e.g. as follows: "all devices j which drop below a battery voltage level of xi shall be flagged to follow-up". The expert system is preferably adapted to update the rule system continuously based on the data analysis.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
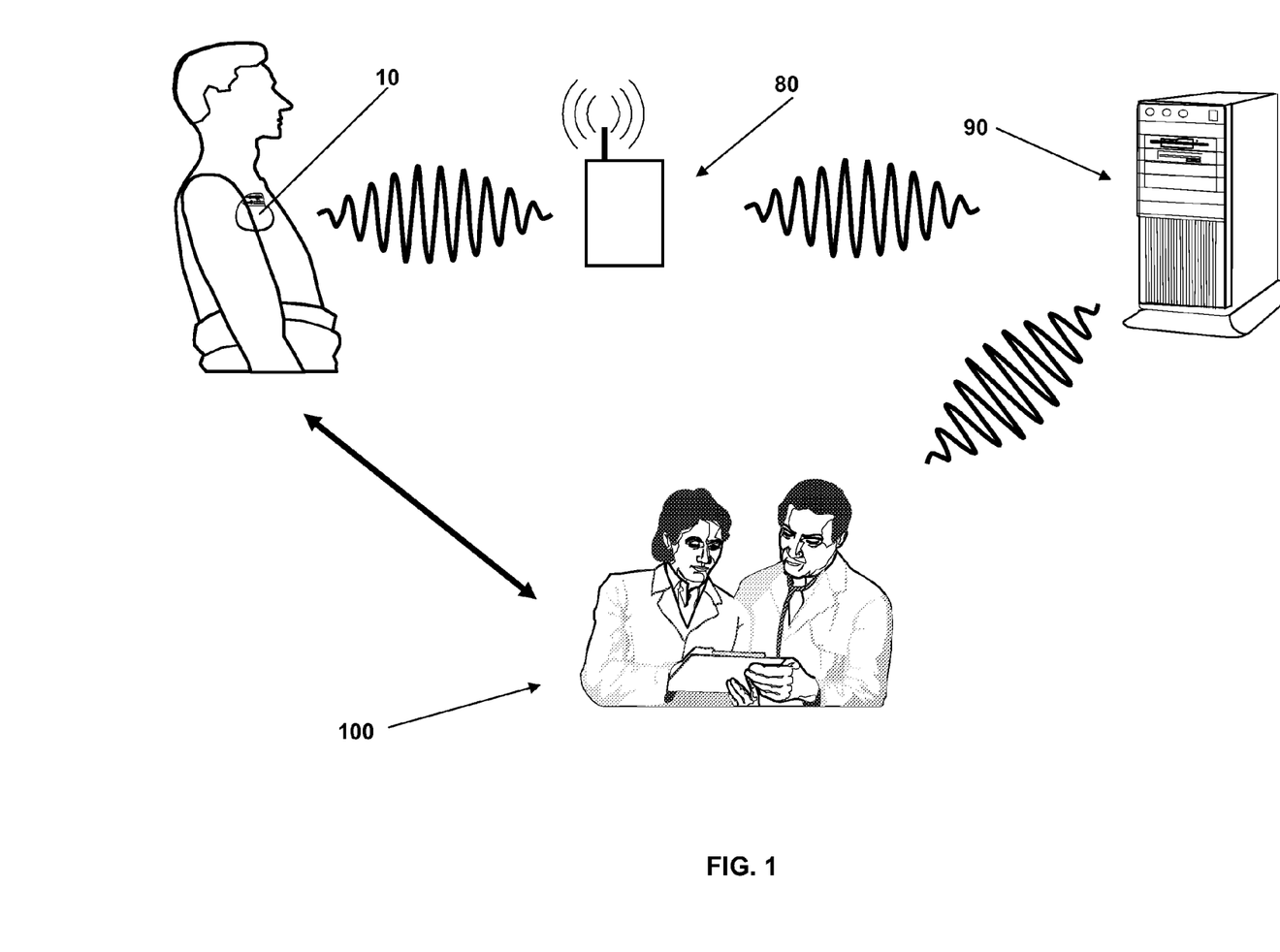
FIG. 1 is a schematic overview over a implantable device system comprising an implantable medical device, an external transceiver device and a service center.

FIG. 1 shows an implantable device system comprising an implantable medical device 10, an external transceiver device 80 and a central service center 90. The implantable medical device 10 is for example an implantable pacemaker or an implantable cardioverter/defibrillator or a device for cardiac resynchronisation. The implantable medical device 10 comprises an implant transceiver for wireless communication with the external transceiver device 80. The external transceiver device 80 comprises an external transceiver unit (not shown) for wireless communication with the implant transceiver unit and a data communication interface (also not shown) adapted to allow a data communication with the service center 90. The data communication interface preferably is adapted to use a public data communication line as a telephone landline connection or wireless connection via GPRS/UMTS or SMS.

The central service center 90 comprises or is connected to a user interface allowing a physician or a team of physicians to interact with the central service center. The user interface may comprise a display for displaying data to the physician 100 and some input device allowing the physician 100 to enter instructions or data into the central service center 90. The central service center 90 further comprises a central database that is connected to said data communication interface (see FIG. 4) and a data evaluation module that is connected to the database that is adapted to evaluate data stored and said database.

Figure 2:
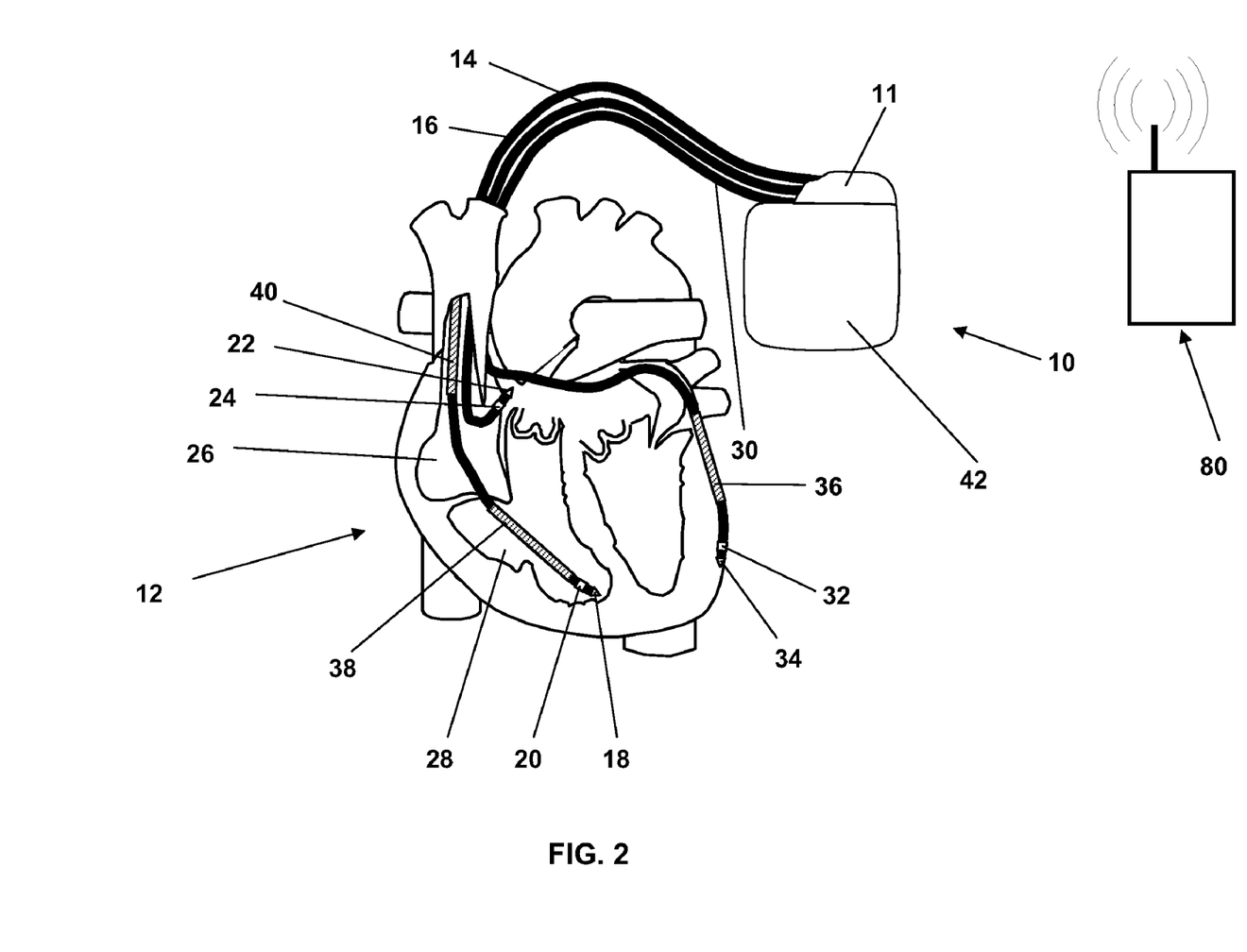
FIG. 2 shows a three chamber bi-ventricular implantable cardioverter/defibrillator (ICD).

In FIG. 2 the implantable medical device is a three chamber biventricular pacemaker and cardioverter/defibrillator 10 that is connected to pacing/sensing leads placed in a heart 12 is illustrated.

Pacemaker 10 comprises a gas proof housing (case) 42 made from a biocompatible metal such as titanium. The case is absolutely water- and airtight. Pacemaker 10 comprises a transparent header 11 that is made from electrically insulating plastic and that encloses terminals to which electrode leads 16, 18 and 30 are connected detachably. Electrode leads 16, 18 and 30 each comprise a proximal connector (not shown) that is plugged into the connectors of header 13.

The implantable medical device 10 is electrically coupled to heart 12 by way of leads 14, 16 and 30.

Lead 14 is a right atrial electrode lead that has a pair of right atrial electrodes 22 and 24 that are in contact with the right atria 26 of the heart 12.

Lead 16 is a right ventricular electrode lead that has a pair of ventricular stimulation and sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Atrial cardioversion shock coil 40 is a coil electrode providing a relatively large geometric area when compared to the stimulation electrodes 18, 20, 22 and 24.

Lead 30 is a left ventricular electrode lead passing through the coronary sinus of heart 12 and having a left ventricular ring electrode LV RING 32 a left ventricular tip electrode LV TIP 34. Further, a left ventricular defibrillation shock coil 36 is arranged on lead 30.

Implantable medical device 10 has a case 42 made from electrically conductive material such as titanium that can serve as a large surface electrode IMD CASE. The case is a gas proof housing and is absolutely water- and airtight.

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

Figure 3:
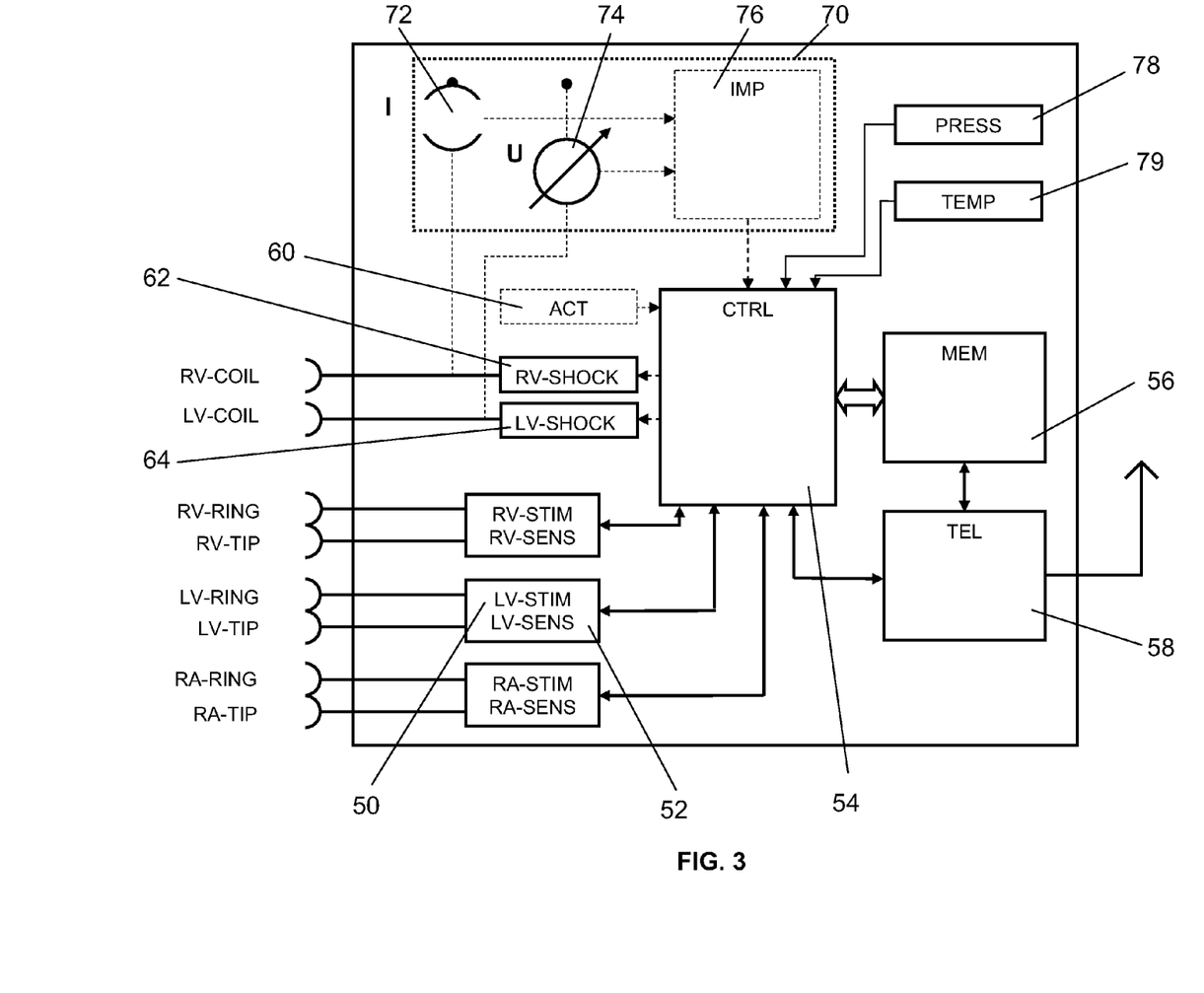
FIG. 3 is a schematic diagram of the device modules of the ICD of FIG. 3.

Referring to FIG. 3 a simplified block diagram of an implantable medical device 10 is illustrated. During operation of the pacemaker leads 14, 16 and 30 are connected to respective output/input terminals of pacemaker 10 as indicated in FIG. 2 and carry stimulating pulses to the tip electrodes 18, 22 and 34 from a right ventricular pulse generator RV-STIM, a right atrial stimulation pulse generator RA-STIM and a left ventricular pulse generator LV-STIM, respectively. Further, electrical signals from the right ventricle are carried from the electrode pair 18 and 20, through the lead 16, to the input terminal of a right ventricular sensing stage RV-SENS; and electrical signals. from the right atrium are carried from the electrode pair 22 and 24, through the lead 14, to the input terminal of a right atrial channel sensing stage RA-SENS. Electrical signals from the left ventricle are carried from the electrode pair 32 and 34, through the lead 30, to the input terminal of a right ventricular sensing stage RV-SENS The atrial channel sensing stage A-SENS and ventricular sensing stages RV-SENS and LV-SENS comprise analog to digital converter (ADC; not shown) that generate a digital signal from electric signals picked up in the atrium or the ventricle, respectively.

Controlling the implantable medical device 10 is a control unit CTRL 54 that is connected to sensing stages A-SENS and V-SENS, to stimulation pulse generators A-STIM and V-STIM and to an impedance determination unit 70. Control unit CTRL 54 comprises a digital microprocessor forming a central processing unit (CPU; not shown) and is— at least in part—controlled by a program stored in a memory circuit MEM 56 that is coupled to the control unit CTRL 54 over a suitable data/address bus ADR.

Control unit CTRL 54 receives the output signals from the atrial sensing stage RA-SENS and from the ventricular sensing stages RV-SENS and LV-SENS. The output signals of sensing stages RA-SENS and RV-SENS are generated each time that a P-wave representing an intrinsic atrial event or an R-wave representing an intrinsic ventricular event, respectively, is sensed within the heart 12. An As-signal is generated, when the atrial sensing stage RA-SENS detects a P-wave and a Vs-signal is generated, when the ventricular sensing stage RV-SENS detects an R-wave.

Control unit CTRL 54 also generates trigger signals that are sent to the atrial stimulation pulse generator RA-STIM and the ventricular stimulation pulse generators RV-STIM and LV-STIM, respectively. These trigger signals are generated each time that a stimulation pulse is to be generated by the respective pulse generator RA-STIM, RV-STIM or LV-STIM. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, RA-SENS, RV-SENS and/or LV-SENS, is typically disabled by way of a blanking signal presented to these amplifiers from the control unit CTRL 54, respectively. This blanking action prevents the sensing stages RA-SENS, RV-SENS and LV-SENS from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event Ars but ignored.

Control unit CTRL 54 comprises circuitry for timing ventricular and/or atrial stimulation pulses according to an adequate stimulation rate that can be adapted to a patient's hemodynamic need as pointed out below.

Now referring to the control unit CTRL 54, this memory circuit MEM 56 allows certain control parameters, used by the control unit CTRL 54 in control-ling the operation of the implantable medical device 10, to be programmably stored and modified, as required, in order to customize the implantable medical device's operation to suit the needs of a particular patient. Such data includes the basic timing intervals used during operation of the pacemaker 10 and AV delay values and hysteresis AV delay values in particular.

Further, data sensed during the operation of the implantable medical device 10 may be stored in the memory MEM 56 for later retrieval and analysis.

A telemetry circuit TEL 58 is further included in the implantable medical device 10. This telemetry circuit TEL 58 is connected to the control unit CTRL 54 by way of a suitable command/data bus. Telemetry circuit TEL 58 allows for wireless data exchange between the implantable medical device 10 and some remote programming or analyzing device which can be part of a centralized service center serving multiple pacemakers.

The implantable medical device 10 in FIG. 3 is referred to as a three chamber pacemaker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage A-SENSE, the atrial stimulation pulse generator A-STIM and corresponding portions of the control unit CTRL 54, are commonly referred to as the atrial channel. Similarly, those portions of the pacemaker 10 that interface with the right ventricle 28, e.g., the lead 16, the R-wave sensing stage V-SENSE, the ventricular stimulation pulse generator V-STIM, and corresponding portions of the control unit CTRL 54, are commonly referred to as the ventricular channel.

In order to be able to detect periods of physical activity of a patient indicating that the patient is awake and in order to allow rate adaptive pacing in a DDDR or a DDIR mode, the pacemaker 10 further includes a physiological sensor ACT 60 that is connected to the control unit CTRL 54 of the pacemaker 10. While this sensor ACT 60 is illustrated in FIG. 2 as being included within the pacemaker 10, it is to be understood that the sensor may also be external to the implantable medical device 10, yet still be implanted within or carried by the patient.

The control unit CTRL 54 is adapted to determine an adequate heart rate or stimulation rate in any manner known as such.

For impedance measurement, impedance determination unit 70 is provided. Impedance determination unit 70 comprises a constant current source 72 that is connected or can be connected to electrodes for intracorporeal placement as shown in FIG. 2. In order to allow for a plurality of impedance measurement electrode configurations, preferably some means of switching is provided between the constant current source 72 and the electrode terminals of the implantable medical device 10. The switch is not shown in FIG. 3. Rather, particular impedance measurement configurations are shown as examples.

Similarly, a impedance measuring unit 74 for measuring a voltage corresponding to a current fed through a body by said constant current source is provided and can be connected to a number of electrodes although a switch for switching between these configurations is not shown in FIG. 3.

As an alternative to constant current source 72 a constant voltage source can be provided. Then, the measuring unit will be adapted to measure a current strength of a current fed through a body by said constant voltage source.

Both, constant current source 72 and impedance measurement unit 74, are connected to an impedance value determination unit 76 that is adapted to determine an impedance value for each measuring current pulse delivered by the constant current source 72.

The impedance value determination unit 76 comprises another analog to digital converter ADC in order to generate a digital impedance signal that is fed to the control unit CTRL 54.

Further, a pressure sensor PRESS 78 for sensing a pressure in the interior of housing 42 and a temperature sensor TEMP 79 for sensing a temperature in housing 42 are provided. Both sensors 78 and 79 are connected to control unit CTRL 54 via an analog to digital converter.

Control unit CTRL 54 further comprises watchdog and reset units to provide safety when the CPU should fail. The watchdog units therefore are designed to operate independently from the CPU of the control unit CTRL 54. In FIG. 3, the watchdog and reset units are not shown.

The control unit 54 is adapted to collect data that represent measurements of one or more values of one or more parameters of the following operational parameters of the battery and/or the electronic module:

peak current consumption, average current consumption, high/low/average voltage level, charge counter for battery status, programmed versus actual pacing voltage in at least 1 pacing channel, programmed versus actual shock energies (if a defibrillation shock generator is available), charging times, impedance of all pacing and shock electrodes, status of embedded software, in particular number of CPU cycles, number of memory accesses, number of resets; number of read/write errors; number of hypo- and hyper-watchdog errors; number of recoverable and non-recoverable memory corruptions, actual service time, temperature, temperature rise during high-voltage operations, pressure, impedance of components such as resistors, capacitors, self-diagnostic information of the IC (e.g. range checks)

and to initiate transmission the data to the external transceiver via said implant transceiver, The external transceiver 80 is adapted to collect automatically data from the implantable medical device 10 and to transmit them to the central service center 90.

Data collection and transmission is performed once a day.

Figure 4:
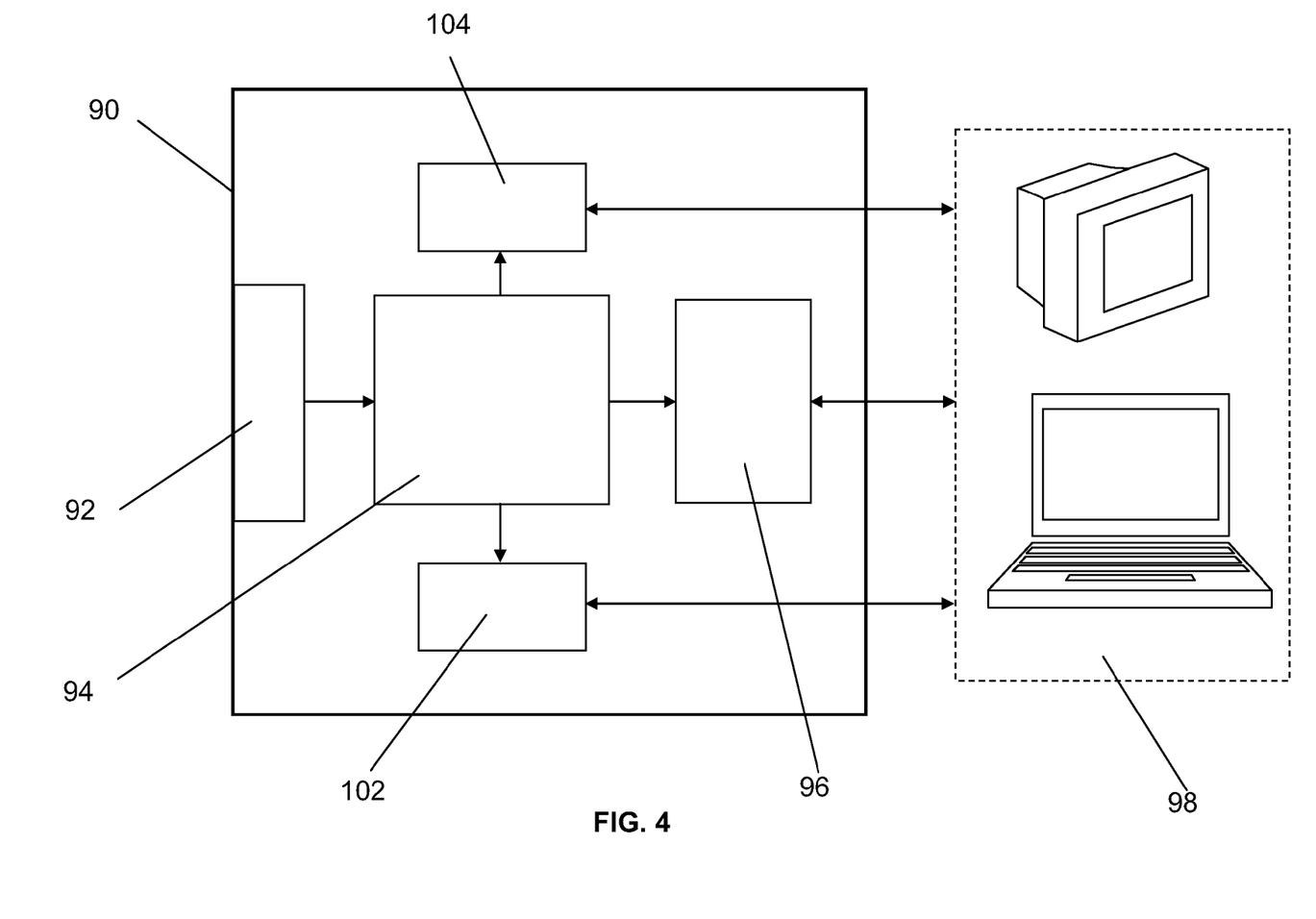
FIG. 4 is a schematic diagram of the service center.

FIG. 4 shows the central service center 90 comprising a data communication interface 92 for communicating with the external transceiver device 80. Connected to the data communication interface 92 is a central database 94 for storing data representing measurements performed by the implantable medical device 10 and the external transceiver device 80. The central database 94 is connected to a data evaluation module 96 that is adapted to evaluate data stored in said database. The evaluation includes data trending of stored data.

Connected to the data analysis module is a user interface 98 for displaying data generated by the data analysis module 96 to a user allowing a user to enter instructions or data for controlling the data analysis module 96.

The data analysis module 96 is adapted to perform a data analysis in four different levels:
(1) Each value against specification;
(2) Each value is trended and checked against unexpected changes (e.g. increase of battery voltage);
(3) Each value is checked if it represents an outlier as compared to all comparable devices (e.g. charging time of one device is within the specification but far outside the normal data population);
(4) Every value is ranked and against values of other devices to identify the worst device.

The data analysis module 96 compares all measurements (currents, voltages, impedance, . . . ) against predetermined specifications and to set a flag for each out-of-spec value if the actual value is outside the predetermined specifications. Further, the data analysis module 96 trends all measurements over time and to set an unexpected change flag in case of detection of any unexpected change, e.g. $dM_i/dt > threshold_i$. Preferably, for values which are not expected to change then a change of >10% is considered significant, that is, an unexpected change flag is set if a change >10% is detected in the trended data.

Further, the data analysis module computes consistency checks, e.g. battery voltage level versus charge counter value, when performing a data analysis according to level (2) or (3).

Also, the data analysis module perform a comparisons between devices if more than 27 comparable devices available. The analysis comprises one or more of the following computations:

For all measurements i of all comparable devices j compute average Ai+standard deviation σi; identify devices, for which measurements are outside 3*σi For all measurements i of all comparable devices j compute the rank Ri; identify devices, for which measurements are >9th percentile Other known statistical techniques to identify outliers Further, the data analysis module performs a comparison of measurements of devices which share same component j, e.g. batteries from vendor A, as follows:

For all measurements i of all comparable components k compute average Ai+standard deviation σi; identify devices, for which measurements are outside 3*σi The service center further comprises a data mining system 102 that can be used if the measurements, trends, averages, etc. represent multidimensional data which need to be condensed more. The data mining system classifies devices which fail one criteria (e.g. voltage level too low), two criteria (e.g. voltage level too low and charging time is increasing over time), etc. to flag devices which fail an increasingly number of criteria The service center further comprises an expert system 104 to further compute the analyzed data. The expert system implements a rule system to identify previously noted problems e.g. as follows: "all devices j which drop below a battery voltage level of xi shall be flagged to follow-up". The expert system updates the rule system continuously based on the data analysis.

Although an exemplary embodiment of the present invention has been shown and described, it should be apparent to those of ordinary skill that a number of changes and modifications to the invention may be made without departing from the spirit and scope of the invention. This invention can readily be adapted to a number of different kinds of implantable medical devices by following the present teachings. All such changes, modifications and alterations should therefore be recognized as falling within the scope of the present invention.

What is claimed is:

1. An implantable device system comprising:
   an implantable medical device;
   an external transceiver device;
   a service center;
   said implantable medical device comprising a battery and an electronic module including
      a stimulation pulse generator configured to generate electric stimulation pulses and being connected or being connectable to at least a ventricular stimulation electrode for delivering electric stimulation pulses to at least a ventricle of a heart;
      at least one sensing stage connected or being connectable to an electrode for picking up electric potentials inside at least a ventricle of a heart, said at least one sensing stage being configured to sense an excitation or a contraction of ventricular myocardium;
      at least one internal sensor that is connected to said battery, said stimulation pulse generator and at least one said sensing stage and that is configured to collect physical data representing values of operational parameters of said battery and said electronic module comprising a control unit;
      said control unit connected to said battery, said stimulation pulse generator and said sensing stage and configured to collect data representing values of operational parameters of said battery and said electronic module including said control unit;
      an implant transceiver unit for wireless communication with said external transceiver device;
   said external transceiver device including
      an external transceiver unit for wireless communication with said implant transceiver unit;
      a data communication interface configured to allow a data communication with said service center;
   said service center including
      another data communication interface configured to allow data communication with said external transceiver device;
      a central database connected to said data communication interface for data storage and automatic data analysis that is configured to store data received from said external transceiver device per implantable medical device over time;
      a data evaluation module connected to said database and configured to evaluate data stored in said database wherein said evaluation includes data trending of stored data;
      a user interface connected to said data evaluation module and being configured to display trended data and to receive user inputs;
   wherein said control unit is configured to
      collect data that represent measurements of one or more values of one or more parameters of following operational parameters of said battery and/or said electronic module: peak current consumption, average current consumption, high/low/average voltage level, charge counter for battery status, programmed versus actual pacing voltage in at least 1 pacing channel, programmed versus actual shock energies (if a defibrillation shock generator is available), charging times, impedance of all pacing and shock electrodes, status of embedded software, in particular number of CPU cycles, number of memory accesses, number of resets; number of read/write errors; number of hypo- and hyper-watchdog errors; number of recoverable and non-recoverable memory corruptions, actual service time, temperature, temperature rise during high-voltage operations, pressure, impedance of components such as resistors, capacitors, self-diagnostic information of an IC, range checks;
      initiate transmission of said data to said external transceiver via said implant transceiver;
   wherein said external transceiver is configured to collect automatically data from said
      implantable medical device and to transmit said data to said central service center;
   wherein said data analysis module is configured to perform a data analysis in four different levels:
      (1) each value against specification;
      (2) each value is trended and checked against unexpected changes;
      (3) each value is checked if it represents an outlier as compared to all comparable devices; and,
      (4) every value is ranked against other devices to identify a worst device,
   wherein said data analysis module is configured to trend all measurements over time and to set an unexpected change flag in case of detection of any unexpected change,
   wherein either
      (1) said data analysis module is further configured to perform a comparison between corresponding measurements of different devices if more than 27 comparable devices are available and wherein said analyzing module is either
         (a) configured to compute for all measurements i of all comparable devices j average Ai+standard deviation σi and identify devices, for which measurements are outside 3*σi, or
         (b) is configured to compute for all measurements i of all comparable devices j compute the rank Ri and identify devices, for which measurements are >9th percentile,
      or
      (2) said data analysis module is configured to compare measurements of devices which share a same component and wherein said data analysis module is configured to compute an average Ai+standard deviation σi for all measurements i of all comparable components k and to identify devices, for which said measurements are outside 3*σi.

2. The implantable device system according to claim 1, wherein said implantable medical device further comprises an impedance determination unit that is connected to said control unit and that comprises:
   a constant current source or a constant voltage source having current feed terminals that are connected or can be connected to electrodes for intracorporeal placement and that is configured to generate sub-threshold measuring current pulses having a constant current strength or a constant voltage, respectively, for causing a current to be fed through a body via intracorporeally placed electrodes;

a measuring unit for measuring a voltage corresponding to a current fed through a body by said constant current source or a current strength of a current fed through a body by said constant voltage source, respectively; and, an impedance value determination unit that is connected to said constant current source or said constant voltage source and said measuring unit that is configured to determine an impedance value for each measuring current pulse.

3. The implantable device system according to claim 1, wherein said external receiver is configured to add data from said external receiver as a data set including data representing measurements relating to at least one value of one or more parameters including:

peak current consumption, average current consumption, high/low/average voltage level, number of charging cycles, number of successful/dropped MICS, number of successful/dropped LLine/SMS/GPRS/UTMS connections, number of corrupted and uncorrupted data packages.

4. The implantable device system according to claim 1, wherein said implantable medical device and said external transceiver are configured to generate and transmit one data set per day.

5. The implantable device system according to claim 1, wherein said data analysis module is configured to compare all measurements against predetermined specifications and to set a flag for each out-of-spec value if an actual value is outside said predetermined specifications.

6. The implantable device system according to claim 1, set an unexpected change flag if a change >10% of a measurement is detected in trended data relating to said measurement.

7. The implantable device system according to claim 1, wherein said data analysis module is further configured to compute consistency checks for interrelated measurements.

8. The implantable device system according to claim 1, wherein said service center further comprises a data mining system that is configured to classify devices which fail one or more criteria.

9. The implantable device system according to claim 1, wherein said service center further comprises an expert system to further compute analyzed data, wherein said expert system implements a rule system to identify previously noted problems.

10. The implantable device system according to claim 9, wherein said expert system is preferably configured to update a rule system continuously based on data analysis.

11. The implantable device system according to claim 1, wherein said user interface is configured to display trended data and to receive user inputs for data retrieval and manipulation.

* * * * *